United States Patent [19]

Mariani et al.

[11] Patent Number: 5,325,704
[45] Date of Patent: Jul. 5, 1994

[54] SURFACE ACOUSTIC WAVE (SAW) CHEMICAL MULTI-SENSOR ARRAY

[75] Inventors: Elio A. Mariani, Hamilton Square; William J. Skudera, Jr., Oceanport, both of N.J.

[73] Assignee: The United States of America as represented by the Secretary of the Army, Washington, D.C.

[21] Appl. No.: 157,847

[22] Filed: Nov. 22, 1993

[51] Int. Cl.⁵ .................. G01N 30/76; G01N 30/78; G01N 30/48
[52] U.S. Cl. .................. 73/24.06; 310/313 B; 310/313 D; 310/313 R; 73/24.01
[58] Field of Search .................. 73/24.06, 24.01; 310/313 B, 313 D, 313 R

[56] References Cited

U.S. PATENT DOCUMENTS

| | | | |
|---|---|---|---|
| 3,981,176 | 9/1976 | Jacobs | 73/24 |
| 4,312,228 | 1/1982 | Wohltjen | 73/24 |
| 4,361,026 | 11/1982 | Muller et al. | 73/24.01 |
| 4,642,506 | 2/1987 | Lewis | 310/313 D |
| 4,759,210 | 7/1988 | Wohljen | 73/23 |
| 4,801,836 | 1/1989 | Mariani | 310/313 D |
| 4,860,573 | 8/1989 | Barendz et al. | 73/24.01 |
| 4,895,017 | 1/1990 | Pyke et al. | 73/23 |
| 4,912,356 | 3/1990 | Mariani et al. | 310/313 D |
| 4,932,255 | 6/1990 | Brace et al. | 73/24.03 |
| 5,012,668 | 5/1991 | Haworth | 73/24.06 |
| 5,051,645 | 9/1991 | Brace et al. | 310/313 D |
| 5,130,257 | 7/1992 | Baer et al. | 436/151 |
| 5,151,110 | 9/1992 | Bein et al. | 55/75 |
| 5,212,420 | 5/1993 | Hickernell et al. | 310/313 D |
| 5,221,871 | 6/1993 | Fuchs et al. | 310/313 R |
| 5,235,235 | 8/1993 | Martin et al. | 310/313 |
| 5,289,073 | 2/1994 | Mariani | 310/313 D |

Primary Examiner—Hezron E. Williams
Assistant Examiner—John David Wiggins
Attorney, Agent, or Firm—Michael Zelenka; William H. Anderson

[57] ABSTRACT

A sensor for chemical vapor detection using a surface acoustic wave (SAW) array that provides a means for simultaneously detecting several chemical agents. The sensor has a piezoelectric substrate and a bidirectional surface acoustic wave transducer on the substrate. Also on the substrate are several pairs of identical acoustic sensing and reference channels each on opposite sides of the transducer in a mirror image fashion. Each channel pair has a thin film capable of absorbing a chemical vapor to be monitored and a metallic surface acoustic wave grating reflector capable of receiving and reflecting surface acoustic waves through the thin film and back to the transducer. An acoustic absorber separates each channel. The reference channels are protected from ambient conditions while the sensing channels are exposed to such conditions. An RF signal is applied to the transducer causing the propagation of an acoustic signal into each of the sensing channels and reference channels. Output signals from the transducer are then detected. The array is preferably in a miniature configuration which is suitable for wearing on a person's wrist or arm.

20 Claims, 3 Drawing Sheets

SURFACE ACOUSTIC WAVE (SAW) CHEMICAL MULTI-SENSOR ARRAY

GOVERNMENT INTEREST

The invention described herein may be manufactured, used and licensed by or for the Government of the United States without the payment to us of any royalty thereon.

BACKGROUND OF THE INVENTION

1. Field of the Invention

The invention relates to sensors for chemical vapor detection using a surface acoustic wave (SAW) array that provides a means for simultaneously detecting several chemical agents. The array is preferably in a miniature configuration which is suitable for wearing on a person's wrist or arm.

2. Description of the Prior Art

It has long been desired to provide a low cost, miniature sensor for the simultaneous detection of multiple chemical agents. U.S. Pat. No. 5,235,235 pertains to multiple-frequency acoustic wave devices for chemical sensing and materials characterization in both gas and liquid phases. A chemical sensor includes two or more pairs of interdigital electrodes having different periodicities. The electrodes are patterned on a surface of a piezoelectric substrate. Each pair of electrodes may launch and receive various acoustic waves, including a surface acoustic wave. The frequencies associated with each are functions of the transducer periodicity as well as the velocity of the particular acoustic wave in the chosen substrate material. An acoustic wave interaction region exists between each pair of electrodes. Circuitry is used to launch, receive, and monitor the propagation characteristics of the acoustic waves and may be configured in an intermittent measurement fashion or in a continuous measurement fashion. Perturbations to the acoustic wave velocity and attenuation are recorded at several frequencies and provide the sensor response. U.S. Pat. No. 5,151,110 relates to a selective chemical sensor for selective detection of chemical entities even at the nanogram level. The sensor comprises a piezoelectric substrate capable of detecting mass changes resulting from adsorption of material thereon and a coating applied to the substrate, which selectively sorbs chemical entities of a size smaller than a preselected magnitude. U.S. Pat. No. 5,130,257 discloses a sensor suitable for use as a viscosity sensor, a chemically selective sensor, or a chemically specific sensor. The sensor is a surface transverse wave device that includes a binding layer selected to bind to the solute to be measured. This binding layer can be an antibody so that the sensor detects a particular antigen. U.S. Pat. No. 4,932,255 discloses flow sensing using surface acoustic waves. A sensor employs a SAW oscillator heated above the ambient by converting RF energy to heat via acoustic dissipation in energy absorbers located outside the path of propagation. The device is used to measure fluid flow, where fluid is directed across the SAW delay line lowering the substrate temperature which is elevated by the heat generating energy absorbers outside the propagation path. The temperature reduction changes the oscillator frequency which is indicative of the gas velocity. In operation, gases are passed across the top of the delay-line while liquids are passed across the bottom of the delay-line in a back-side sensing operation. To measure gas or vapor contaminants, chemically sensitive coatings placed on the substrate in the propagation path can be used to sense contaminants in a gas flowing over the substrate. U.S. Pat. No. 4,759,210 relates to an apparatus and method of monitoring a gas by simultaneously flowing the gas through means for trapping gaseous species. Each of the trapping means is selective in trapping gaseous species and differs from the selectivity of the others. Each is subjected to conditions to effect release of any gaseous species trapped while maintaining the other means in a condition suitable for selective trapping of gaseous species. The gas issuing from the trapping means is contacted with means for sensing gaseous species. Each sensing means is adapted so that its selectivity to sensing gaseous species differs from such selectivity of the other sensing means.

In contrast to the above, the inventive SAW based chemical multisensor array provides a low cost, miniature configuration for the detection of several chemical agents simultaneously. By using the multichannel SAW device in combination with a simple read-out circuit, detection of a particular chemical agent or agents is indicated.

SUMMARY OF THE INVENTION

The invention provides a surface acoustic wave, multi-channel sensor which comprises a piezoelectric substrate and a bidirectional surface acoustic wave transducer disposed on the substrate. It has a plurality of pairs of acoustic sensing and reference channels with each pair member being substantially identical to its corresponding other pair member. The sensing channels are sequentially disposed on the substrate in juxtaposition with one side of the transducer and the reference channels are sequentially disposed on the substrate in juxtaposition with the other side of the transducer. Each respective sensing channel and reference channel pair sequentially comprise a thin film whose composition is capable of absorbing a chemical vapor to be monitored, and a metallic surface acoustic wave grating reflector capable of receiving incident surface acoustic waves transmitted by the transducer through the thin film and reflecting them back again into the thin film to the transducer. For each channel pair, the reflector grating and thin film is spaced equidistantly from the center line of the bidirectional transducer such that each respective sensing channel and reference channel pair is a mirror image of the other. An acoustic absorber is disposed on the substrate between each sensing channel and each reference channel. Means are provided for protecting each of the reference channels from ambient conditions and simultaneously exposing each of the sensing channels to ambient conditions. Means are also provided for applying an RF signal to the transducer which causes the propagation of an acoustic signal into each of the sensing channels and reference channels. Means are still further provided for detecting output signals from the transducer.

The invention also provides a method for detecting chemical contamination which comprises the steps of providing the above described surface acoustic wave, multi-channel sensor; applying an RF signal to the transducer and causing the radiation of an acoustic signal into each of the sensing channels and reference channels; and detecting and comparing output signals from the transducer.

DETAILED DESCRIPTION OF THE PREFERRED EMBODIMENT

Figure 1:
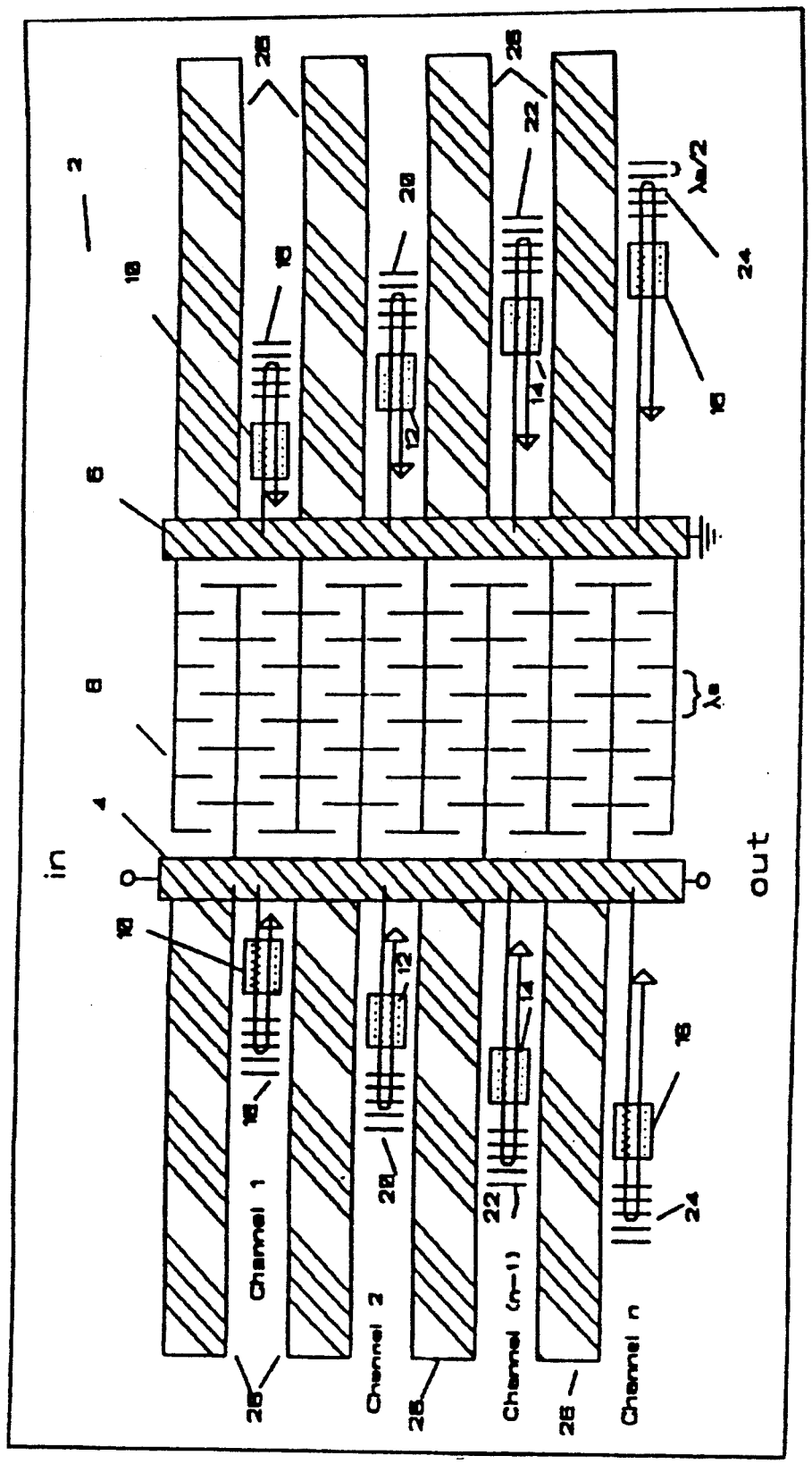
FIG. 1 shows a schematic (not to scale) representation of a surface acoustic wave (SAW) multi-channel sensor array.

FIG. 1 shows a schematic representation of a surface acoustic wave (SAW) multi-channel sensor array. It is noted that FIG. 1 is not drawn to scale. The particular dimensions such as length, width and spacing of the various elements have been exaggerated for purposes of illustration. It is shown to have n-channels arranged on both sides of a single, bidirectional, segmented SAW transducer. The sensor is composed of a substrate 2 of a piezoelectric material. Such piezoelectric materials non-exclusively include polished quartz, lithium niobate, and lithium tantalate, among others. The dimensions of the substrate typically range from about 0.25 to about 2 inches in length and width and from about 0.01 to about 0.03 inch in thickness. Disposed on the surface of the substrate is a SAW transducer which is composed of a pair of summing bus bars 4 and 6 separated by an electrode array 8. The spacing between adjacent interdigitated fingers of the electrode array is a quarter of the wavelength of the applied acoustic wave $\lambda a$. Bus bars 4 and 6 as well as array 8 are composed of a thin layer of a metal having a thickness of from about 500 to about 2,000 angstroms. It is preferably composed of a metal such as aluminum, gold or aluminum alloyed with a small amount of copper. These can be formed by vapor depositing the metal layer and patterning by photolithographic imaging and etching techniques which are well known to those skilled in the art. Bus bar 4 is provided with an input terminal suitable for receiving RF excitation pulses and an output terminal suitable for cooperating with a detector circuit as will be hereinafter described. Bus bar 6 is grounded. Each side of the transducer is provided with a series of n-channels, each having a sensing portion and a reference portion. Each channel is composed of a pair of polymeric films 10, 12, 14 and 16 whose composition is tailored to absorb a particular chemical vapor whose presence is to be monitored. Such polymeric films may be composed of such exemplary materials as poly(epichlorohydrin), polyisobutylene and fluoropolyols, the latter of which is sensitive to organophosphorus gas such as mustard gas. Such polymeric films may be airbrush deposited onto the substrate in close proximity to the transducer. It is important that the dimensions of the polymeric film be carefully controlled since such regulate sensor performance. The polymeric films typically have an approximate length and width of from about 0.01 to about 1.0 inch, or preferably from about 0.1 to about 0.25 inch, although they can be slightly shorter or longer., Their preferred thickness ranges from about 2,000 to about 6,000 angstroms. The thickness of the film can be controlled by measuring the response frequency with the SAW device. The exact length of the chemically absorbing film controls whether the reflected waves to be compared are in phase or out of phase.

Also deposited on the substrate are series of reflective gratings 18, 20, 22 and 24 which serve to reflect the acoustic waves propagated by the transducer on the piezoelectric material. Such gratings comprise a series of metal lines made of the same material as the bus bars 4 and 6 as well as electrode array 8, and are usually formed simultaneously therewith by the same deposition and photoetching process. The center to center spaces between each of the metal lines of the reflective gratings are one-half the wavelength of the applied acoustic wave as shown in FIG. 1 for one of the gratings. Separating each channel is a stripe of an acoustically absorbing material 26. Such absorbing material may be a substance such as rubber, silicone, room temperature vulcanizable material (RTV) or the like. The thickness of the acoustic absorber stripe is not critical and can typically be applied with a syringe or the like. Its purpose is to provide acoustic insulation between each channel and to prevent interference between channels where one does not want crosstalk. The arrow paths indicated at each channel represent the acoustic propagation track for that channel. The incident acoustic wave is generated by the transducer and each reflected wave is produced by the reflective gratings. The mirror image reference and sensing channels are initially calibrated to provide the same output signal for the uncontaminated polymeric film material. The reference channels on the right side are shielded from possible contamination while the sensing channels on the left side are exposed to the ambient condition to be monitored. In the preferred embodiment, each channel operates at the same RF frequency, although they may optionally operate at different frequencies. A preferred operating range is from about 100 to about 1,000 megahertz. Each has a unique path length and corresponding delay time. The sensor array uses alternate channels, that is, alternate segments of the SAW transducer in order to provide channel isolation. Each operational channel has a pair of essentially identical, selectively absorbing thin films, followed by a metallic SAW grating reflector. Each combination of reflector grating and absorbing film is spaced equidistantly from the center line of the bidirectional SAW transducer such that each half of the channel is a mirror image of the other. Preferably, the reflective gratings use the same metallization and thickness as the SAW transducer. Acoustic power in the alternate inactive channels is absorbed using an appropriate material as mentioned above. The multi-sensor array has a right and left grouping of channels such that one group acts as reference channels and the other as sensing channels. Each channel is designed to react to a specific chemical agent by means of the selected thin film polymer coatings for the acoustic vapor sensing function.

Figure 2:
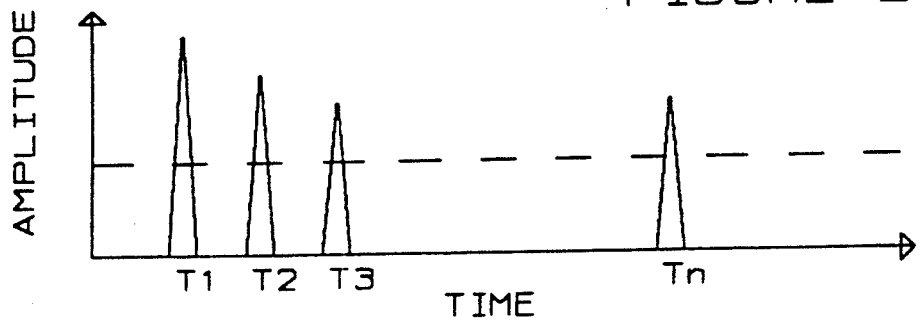
FIG. 2 shows a graph of delayed coherent output signals with no detected channel.
Figure 3:
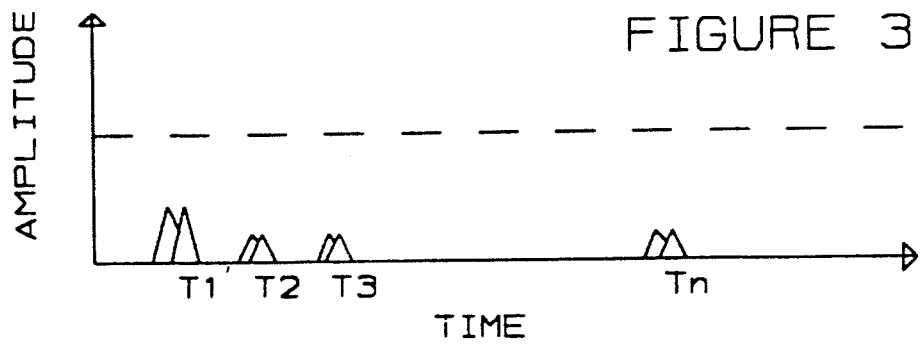
FIG. 3 shows a graph of delayed out of phase output signals with no detected channel.
Figure 4:
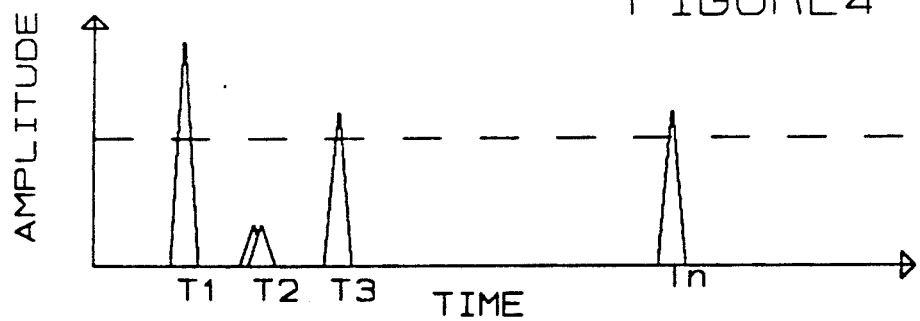
FIG. 4 shows a graph of delayed coherent output signals with detection at T2.
Figure 5:
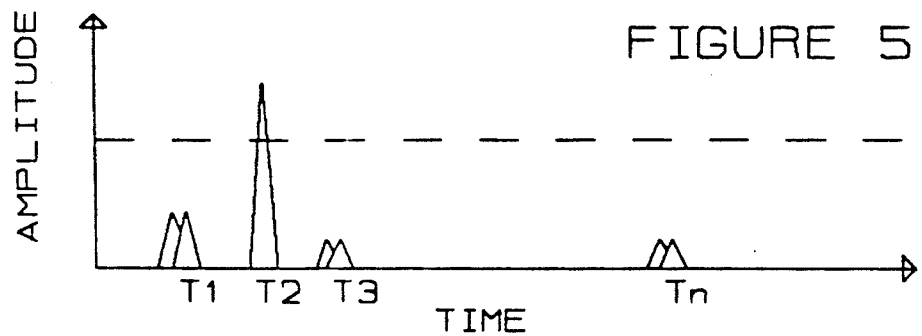
FIG. 5 shows a graph of delayed out of phase signals with detection at T2.
Figure 6:
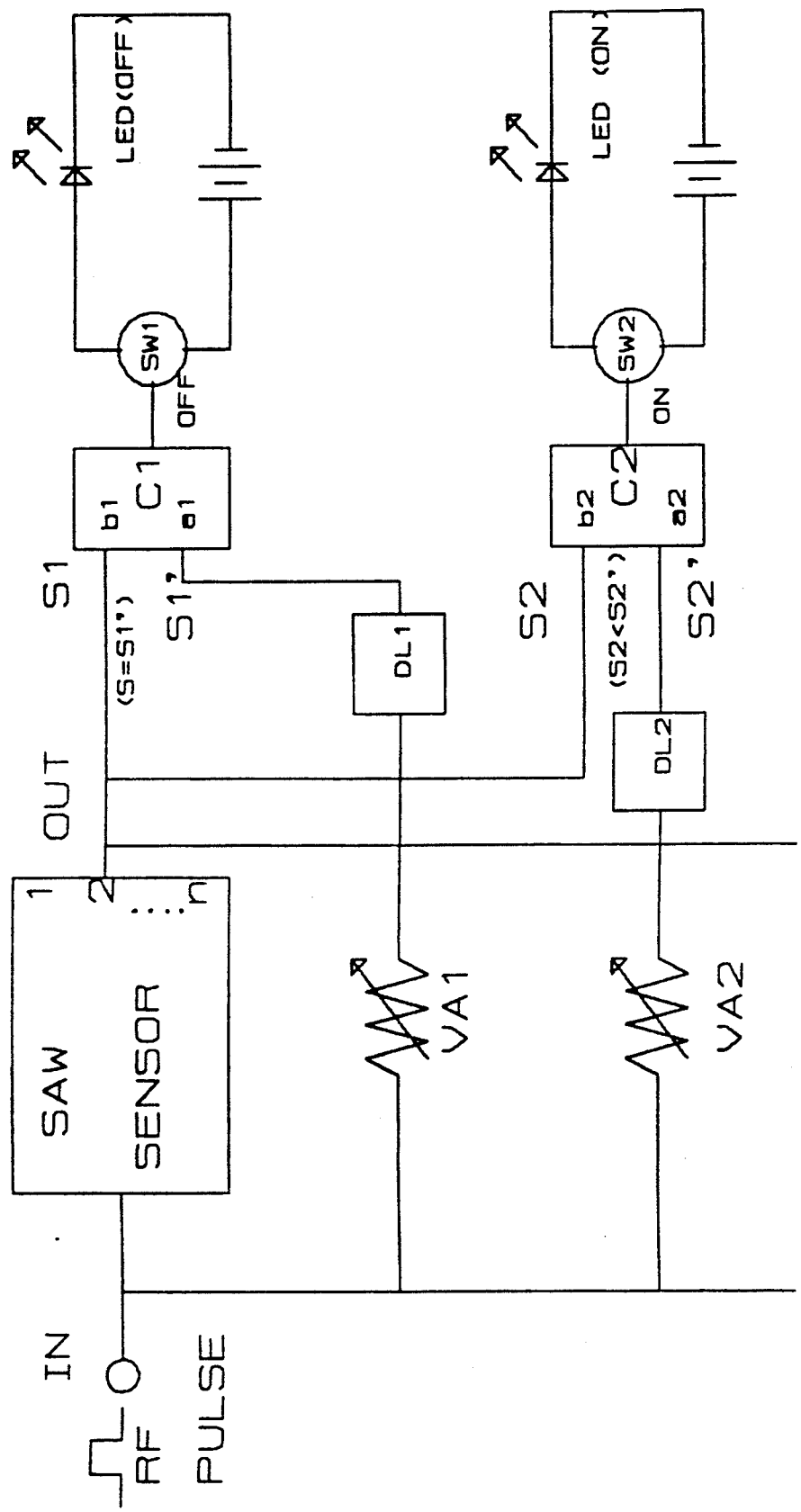
FIG. 6 shows a detector circuit useful for the invention.

Before any channel is exposed to chemical contamination, each channel within the sensor array operates as follows. An input RF pulse excites the SAW transducer, which then generates an acoustic signal into all channels. These signals propagate through the thin film polymer areas and are then reflected by the gratings at the end of each channel. In one embodiment of the invention, these reflected signals are designed to remain electrically in-phase at the transducer output. That is, they add coherently. The output signals are distinguished from each other and the input signals by their position in time. Any subsequent reflections resulting from multiple reflections are greatly attenuated and can be ignored. Since each channel has a different delay time, the output signals emerge as a time ordered sequence of pulses but with only slightly attenuated amplitudes to account for propagation loss. The longer the travelled path, the greater the loss. The output pulses can be arranged to emerge, for example, in one microsecond intervals. However, all output signals would have an amplitude above a certain threshold (dotted line) as shown in FIG. 2. It should be noted that the length of the thin film polymer can be adjusted in each channel to maintain phase coherence. Alternatively, the reflected signals from the right and left side of each channel can be designed to be out of phase by 180° and cancel yielding little or no output. In this case, there would be no detectable signal above some established threshold (dotted line), as shown in FIG. 3. Any small phase adjustment in the propagation paths can be achieved by small changes in the length of the thin film polymers. Any particular sensing channel reacts selectively to a certain chemical agent on the sensing channel side since it is exposed to possible contamination, while the reference side is protected and unaffected. In addition, more than one sensing channel can be made to react, thereby providing multiple sensor capabilities. The sorption of the chemical agent by the thin film polymers while in the gas phase causes a change in the acoustic velocity due to a change in mass loading. This velocity change in the sensing channel alters the previously established phase conditions. As a result, for the case of the in-phase condition, the reflected signals in a given channel is disrupted and the output signal associated with that case will be spread and reduced in amplitude. This reduced output signal corresponds to a particular slot time and indicates detection of a specific chemical agent in that channel. Thus the signal, T2, is below the indicated threshold level (dotted line) and is distinguishable from all others as seen in FIG. 4. In the out of phase case shown in FIG. 5, the phase condition is again disrupted by a change in the acoustic velocity due to the sorption of a chemical agent. Therefore the reflected signals from the opposite sides of the channels no longer cancel and the output signal level increases above the established threshold (dotted line). The high level signal distinguishes the detection channel in this case. Once the output signals from the SAW multichannel chemical sensor are generated, a relatively simple circuit can be used to indicate the channel outputs. Using the circuit shown in FIG. 6, it is possible to complete the detection process to complement the detection function for the in-phase case. FIG. 6 shows a SAW sensor which is activated by an RF input pulse. The output signals S1, S2... are applied to comparators C1, C2... The original input RF pulse is treated by variable attenuators VA1, VA2... to establish a relative amplitude level and delay lines DL1, DL2... which adjust the time delay in parallel branches of the comparator circuit to yield signal S1', S2'... The delay lines delay the signal for from about 0.5 to about 2 microseconds. The delay lines are typically formed on the same substrate as the SAW device and are composed of the same metallic material as the SAW device etched onto the substrate. In the alternative, the RF signal can be converted into a video output and then commonly available video delays lines can be employed. When a signal such as S1 equals its corresponding S1', the comparator output is negative and the latching switch SW1 is in the "off" position. When a signal such as S2 is less than S2', the comparator is non-zero and its respective latching switch SW2 is in the "on" position which turns on the light emitting diode. Battery power is shared for all LED circuits and the balance of the system.

In operation, a RF pulse is applied to the SAW input transducer which generates acoustic waves. These waves traverse through the polymeric film materials and are reflected back by the reflective gratings. The reflected waves from the sensing and reference channels are compared to a threshold detection level in the detection circuit. If the chemical vapor being monitored is absent, the waves travel through the corresponding polymeric films in the given channel at the same velocity and a comparison of the reflected waves will indicate a zero velocity difference, or no contamination. If however, the chemical vapor is present, it will react with the polymeric film, the waves travel through the corresponding polymeric films in the given sensing and reference channels at a different velocity and a comparison of the reflected waves will indicate a non-zero velocity difference, or the presence of contamination. As can be seen in FIG. 1, each channel has a different path length and hence the wave travel time for each channel is different and distinct. Therefore several channels can be monitored with a single transducer output since each channel can be distinguished by the timing of its output signal.

What is claimed is:

1. A surface acoustic wave, multi-channel sensor which comprises a piezoelectric substrate; a bidirectional surface acoustic wave transducer disposed on the substrate; a plurality of pairs of acoustic sensing and reference channels, each pair member being substantially identical to its corresponding other pair member, the sensing channels being sequentially disposed on the substrate in juxtaposition with one side of the transducer and the reference channels being sequentially disposed on the substrate in juxtaposition with the other side of the transducer; each respective sensing channel and reference channel pair sequentially comprising a thin film whose composition is capable of absorbing a chemical vapor to be monitored, and a metallic surface acoustic wave grating reflector capable of receiving incident surface acoustic waves transmitted by the transducer through the thin film and reflecting them back again into the thin film to the transducer; for each channel pair, the reflector grating and thin film is spaced equidistantly from the center line of the bidirectional transducer such that each respective sensing channel and reference channel pair is a mirror image of the other; an acoustic absorber disposed on the substrate between each sensing channel and each reference channel; means for protecting each of the reference channels from ambient conditions and simultaneously exposing each of the sensing channels to ambient conditions; means for applying an RF signal to the transducer which causes the propagation of an acoustic signal into each of the sensing channels and reference channels; and means for detecting output signals from the transducer.

2. The sensor of claim 1 wherein the piezoelectric substrate comprises a material selected from the group consisting of polished quartz, lithium niobate, and lithium tantalate.

3. The sensor of claim 1 wherein the acoustically absorbing material is selected from the group consisting of rubber, silicone, and room temperature vulcanizable material.

4. The sensor of claim 1 wherein the thin film comprises a material selected from the group consisting of poly(epichlorohydrin), polyisobutylene and fluoropolyols.

5. The sensor of claim 1 wherein the thin film material has a thickness of from about 2,000 to about 6,000 angstroms.

6. The sensor of claim 1 wherein the thin film material has a length and width ranging from about 0.01 to about 1.0 inch.

7. The sensor of claim 1 wherein the surface acoustic wave transducer comprises a layer of a metal having a thickness of from about 500 to about 2,000 angstroms.

8. The sensor of claim 1 wherein the surface acoustic wave transducer comprises aluminum, gold or aluminum alloyed with copper.

9. The sensor of claim 1 wherein the piezoelectric substrate has a length and width ranging from about 0.25 to about 2.0 inches and a thickness of from about 0.01 to about 0.03 inch.

10. A method for detecting chemical contamination comprising the steps of:
   A.) providing a surface acoustic wave, multi-channel sensor which comprises
      a.) a piezoelectric substrate;
      b.) a bidirectional surface acoustic wave transducer disposed on the substrate;
      c.) a plurality of pairs of acoustic sensing and reference channels, each pair member being substantially identical to its corresponding other pair member, the sensing channels being sequentially disposed on the substrate in juxtaposition with one side of the transducer and the reference channels being sequentially disposed on the substrate in juxtaposition with the other side of the transducer; each respective sensing channel and reference channel pair sequentially comprising a thin film whose composition is capable of absorbing a chemical vapor to be monitored, and a metallic surface acoustic wave grating reflector capable of receiving incident surface acoustic waves transmitted by the transducer through the thin film and reflecting them back again into the thin film to the transducer; for each channel pair, the reflector grating and thin film is spaced equidistantly from the center line of the bidirectional transducer such that each respective sensing channel and reference channel pair is a mirror image of the other;
      d.) an acoustic absorber disposed on the substrate between each sensing channel and each reference channel;
      e.) means for protecting each of the reference channels from ambient conditions and simultaneously exposing each of the sensing channels to ambient conditions;
      f.) means for applying an RF signal to the transducer which causes the propagation of an acoustic signal into each of the sensing channels and reference channels;
      g.) means for detecting output signals from the transducer; and
   B.) applying an RF signal to the transducer and causing the propagation of an acoustic signal into each of the sensing channels and reference channels; and
   C.) detecting output signals from the sensing channels and the reference channels via the transducer.

11. The method of claim 10 wherein the RF signal has a frequency ranging from about 100 to about 1,000 megahertz.

12. The method of claim 10 wherein the output signals from the sensing channels and the reference channels are coherent.

13. The method of claim 10 wherein the output signals from the sensing channels and the reference channels are out of phase.

14. The method of claim 10 wherein the output signals from the sensing channels and the reference channels are 180° out of phase.

15. The method of claim 10 wherein the piezoelectric substrate comprises a material selected from the group consisting of polished quartz, lithium niobate, and lithium tantalate.

16. The method of claim 10 wherein the acoustically absorbing material is selected from the group consisting of rubber, silicone, and room temperature vulcanizable material.

17. The method of claim 10 wherein the thin film comprises a material selected from the group consisting of poly(epichlorohydrin), polyisobutylene and fluoropolyols.

18. The method of claim 10 wherein the thin film material has a thickness of from about 2,000 to about 6,000 angstroms and a length and width ranging from about 0.01 to about 1.0 inch.

19. The method of claim 10 wherein the surface acoustic wave transducer comprises a layer of a metal having a thickness of from about 500 to about 2,000 angstroms.

20. The method of claim 10 wherein the surface acoustic wave transducer comprises aluminum, gold or aluminum alloyed with copper.

* * * * *